United States Patent [19]
Young et al.

[11] Patent Number: 6,110,125
[45] Date of Patent: Aug. 29, 2000

[54] INDICATING METHOD FOR MENSTRUATION

[75] Inventors: Shuenn-Tsong Young, Taipei; San-Bao Lin, Hsinchu, both of Taiwan

[73] Assignee: Opto Tech Corporation, Hsinchu, Taiwan

[21] Appl. No.: 09/186,635

[22] Filed: Nov. 6, 1998

[30] Foreign Application Priority Data

Oct. 19, 1998 [TW] Taiwan ................................ 87117284

[51] Int. Cl.$^7$ .................................................. A61B 10/00
[52] U.S. Cl. ............................................................. 600/551
[58] Field of Search ............................ 600/549, 551, 600/559, 591

[56] References Cited

U.S. PATENT DOCUMENTS

| | | | |
|---|---|---|---|
| 4,443,851 | 4/1984 | Lin | 600/551 |
| 4,465,077 | 8/1984 | Schneider | 600/551 |
| 4,530,366 | 7/1985 | Nessi et al. | 600/551 |
| 5,216,599 | 6/1993 | Uebe et al. | 600/551 |
| 5,458,121 | 10/1995 | Harada | 600/549 |

*Primary Examiner*—Max Hindenburg
*Attorney, Agent, or Firm*—Bacon & Thomas, PLLC

[57] ABSTRACT

The present invention provides an indicating device for menstruation that is easy to utilize, fast and accurate in measuring temperatures. It comprises: a temperature measuring sensor to measure basal body temperatures of a user and output the measured values; a parameter-inputting means for inputting user-inputting parameters; a microprocessor for storing the basal body temperatures from the temperature measuring sensor, and storing the user-inputting parameters from the parameter-inputting means, then using a mathematical method to estimate the user's monthly gynecophysiological factors in accordance with the basal body temperatures and the user-inputting parameters; and a display means to display the user's monthly gynecophysiological factors estimated by the microprocessor. The indicating device for menstruation uses a mathematical method including weighting coefficients to estimate a user's monthly gynecophysiological factors more accurately.

5 Claims, 4 Drawing Sheets

INDICATING METHOD FOR MENSTRUATION

BACKGROUND OF THE INVENTION

1. Field of the Invention

The present invention relates to an indicating device for menstruation, and more particularly to an indicating device that uses a mathematical method containing weighting coefficients to estimate user's monthly gynecophysiological factors.

2. Description of the Prior Art

Ovulation prediction is important both from the view point of contraception and enhancing fertility.

In respect to enhancing fertility, a woman who wishes to become pregnant has two main alternatives. She can take ovulation-enhancing drugs that have significant side effects; or she can predict the time of ovulation and intercourse at that time for the purpose of conception. One method of detecting and timing ovulation that is simple and well known is recording the basal body temperatures (BBTs) when a woman is waking at morning. This method is based on the fact that a rise in temperature indicates that ovulation has occurred.

The problems with the BBT method are illustrated as follows. The reliability of the BBT method is doubtful, because its effectiveness depends on how accurately the temperature is measured, how carefully the temperature is recorded, and how well this temperature correlates with the actual time of ovulation. This is because only a small rise (about 0.3 to 0.5° C.) occurs in the BBT at the time of ovulation, so an inaccurate value may be obtained unless the measurement and the recording are performed carefully. Moreover, a rise in the BBT dose not always indicate an occurrence of ovulation, for example an infected inflammation will cause a small rise in the BBT. In addition, for a woman desiring to become pregnant, indicia for fertility status (a rise in the BBT) does not occur until the peak time of fertility is almost over.

Some researchers believe that the best fertile time of an ovum may not be more than 12 hours. However, spermatozoa are thought to be viable up to 72 hours in the female genital tract. For a woman desiring to become pregnant, it definitely would be advantageous to know several days ahead when ovulation will occur.

On the other hand, contraception is needed for a woman who does not want to become pregnant. Various natural methods of contraception are referred to as the safe period, this method usually requires that couples abstain from intercourse for at least eight days approximately at midcycle between the menses. It is thought that the ovum released from the ovary is susceptible to fertilization for only 12 hours; and that the spermatozoa deposited in the female reproductive tract are capable of fertilizing the ovum for only 72 hours. Thus, if intercourse did not occur just before and during this period, the spermatozoa could not fertilize the ovum and conception could not take place. This in theory, is a safe and simple method of contraception.

However, in practice, the safe period method has some difficulties. If a woman has regular menstrual cycles, then this method is reliable, because she can readily know from the calendar the safe days after and before ovulation and restrict intercourse accordingly. But menstrual and/or ovulation cycles in many women are often irregular, for example, the menstrual cycle may vary as long as 7 to 13 days for the peak reproductive years and by even greater margins for girls in their teens and women approaching menopause. It is not completely reliable to predict the ovulation time by simply estimating from the estimated next menstrual commence day.

Besides, contraceptive methods also include the BBT method. The BBT method as mentioned above has one drawback that its reliability depends on several factors. In addition, this method has another drawback that it cannot predict in advance when ovulation will take place. Thus the BBT method of contraception is effective after ovulation and so abstinence is required for about two weeks out of each menstrual cycle.

Further, conventional methods of measuring the BBTs are to measure the axillary, oral, vaginal, or rectal temperature by using a mercury or an electronic thermometer; in which the vaginal temperature or the rectal temperature are more representative of the real body temperature, but their measurements are inconvenient; the axillary temperature or the oral temperature can be conveniently measured, but their accuracy is influenced by the possibility of differences in measuring positions and measuring time intervals. In addition, frequent measurements of body temperatures are required in the BBT method, and the temperature detection must be conducted for more than 5 minutes, thus making it very inconvenient to use.

SUMMARY OF THE INVENTION

Therefore, one object of the present invention is to provide an indicating device for menstruation which is easy to utilize, fast to obtain a measuring value, and totally innocuous to the human body. The time and days required to measure the body temperature are drastically decreased, and the measuring values are very accurate.

In order to achieve this object, the indicating device for menstruation of the present invention comprises:

a temperature measuring sensor to measure basal body temperatures of a user and to output the measured values;

a parameter-inputting means for inputting user-inputting parameters;

a microprocessor for storing the basal body temperatures from the temperature measuring sensor, and storing the user-inputting parameters from the parameter-inputting means, then using a mathematical method to estimate the user's monthly gynecophysiological factors in accordance with the basal body temperatures and the user-inputting parameters; and a display means to display the user's monthly gynecophysiological factors estimated by the microprocessor.

The other object of the present invention is to provide an indicating device for menstruation that is equipped with a mathematical method program for predicting and indicating the user's monthly gynecophysiological factors.

It is more accurate to estimate a user's monthly gynecophysiological factors by using the stored mathematical method than by conventional methods. It is therefore more convenient for both enhancing fertility or contraception.

The mathematical method determines the weighting coefficients in accordance with the following principles and uses the determined weighting coefficients to estimate gynecophysiological factors: (1)The weighting coefficient of the newest record is the largest, and the older the historical parameters are, the lesser will be their weighting coefficients; (2) Those which deviate more from the normal range have lesser weighting coefficients whereas those within the normal range have the same weighting coefficients; (3)

When specific events are confirmed by the user, the weighting coefficients obtained by the system will be 0.

BRIEF DESCRIPTION OF DRAWINGS

The above and other objects, advantages and features of the present invention will become apparent from the following description with reference to the accompanying drawings that illustrate examples of the present invention, in which.

DESCRIPTION OF THE PREFERRED EMBODIMENT

Figure 1:
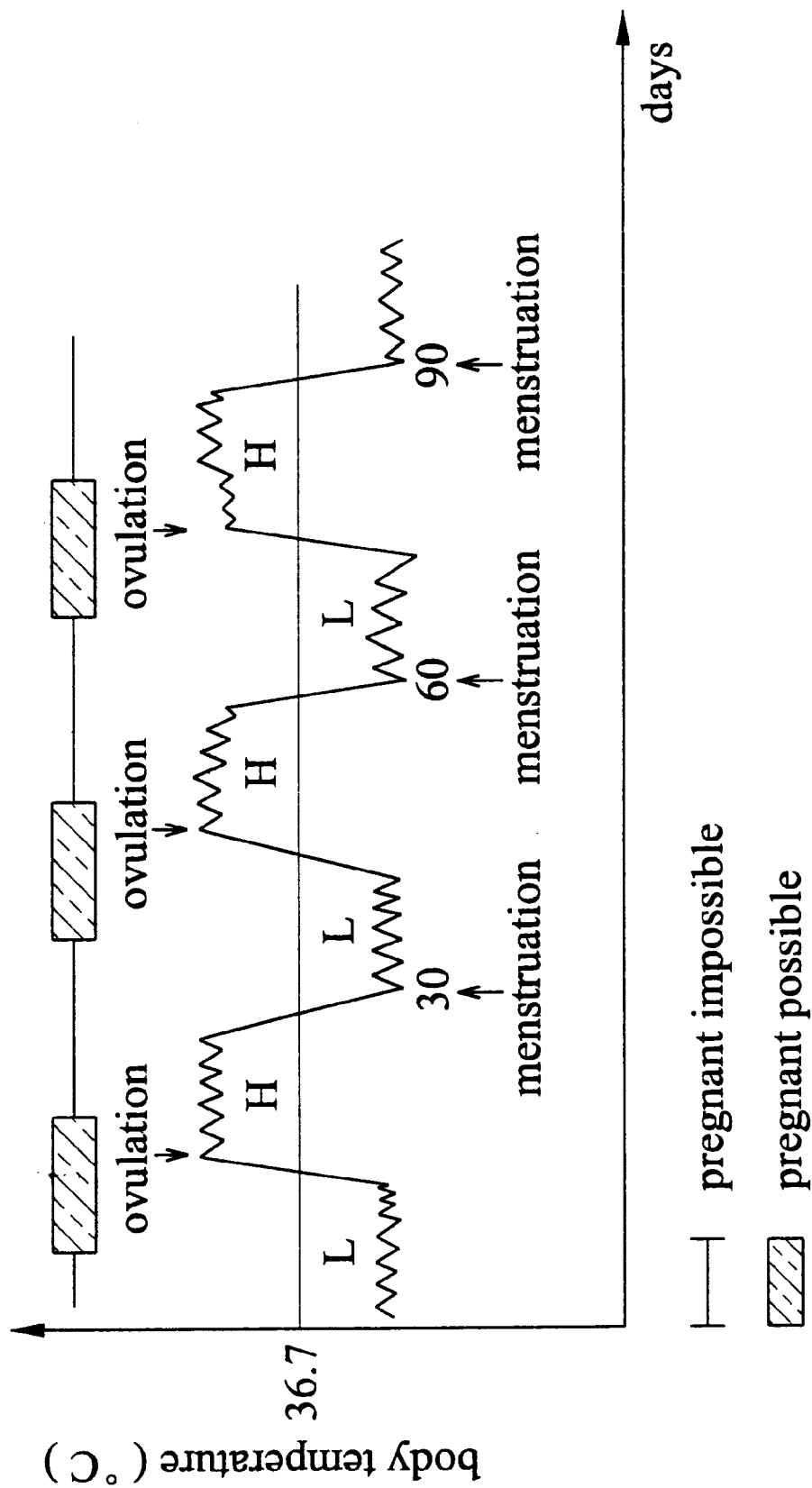
FIG. 1 is a graph showing daily changes in basal body temperatures.

Referring to FIG. 1, there is shown a graph of the basal body temperature of a woman, showing how her temperature fluctuates over about 90 days. The menstrual cycle of this woman can be seen from the graph to be about 30 days long. Temperature rises when ovulation occurs, and falls when menstruation commences. The basal body temperature of a woman can slightly be over or below normal, depending on the individual. However, if a temperature of 36.7° C. is taken as a standard, a normal woman has a repetitive two-phase cycle. The two-phase curve includes two phases respectively designated by L and H, in which the lower temperatures of the cycle are referred to as the low-temperature phase represented by L, and higher temperatures are referred to as the high-temperature phase represented by H. Since the ova and spermatozoa can survive for a certain period, a woman can become pregnant during several days around ovulation.

One object of the present invention is to provide a method and apparatus that accurately predicts when ovulation will occur. Accurate predictions of a user's monthly gynecophysiological factors are made on the basis of a variety of parameters, which are specifically related to the user. These parameters comprise: (1) basal body temperatures, (2) menstrual commence days, (3) vaginal mucus changes and (4) events; in which the basal body temperatures are received by the microprocessor directly after measurements and the user only needs to input the three parameters (2), (3), and (4). It is to be noted that the three parameters may include historical parameters except the input parameters of the present month. In addition, the microprocessor can receive the measured BBTs through a wire or wirelessly. Measuring BBTs for determining the time of ovulation has already been discussed in the description of the prior art. Vaginal mucus changes refer to changes in the cervical mucus from a dry, thick consistency to a watery, more elastic consistency. It has been established that most women can sense this monthly change if they are aware of it. Since this change occurs a few days prior to ovulation, its occurrence when properly combined with parameters (1) and (2) above, can serve as a basis for accurate forecast of ovulation. In addition, parameter (4) is for the system to judge the accuracy of a rise in the basal body temperature, and whether these data serve as a basis for estimating the reference data of the user's monthly gynecophysiological factors when they become historical parameters.

Figure 2:
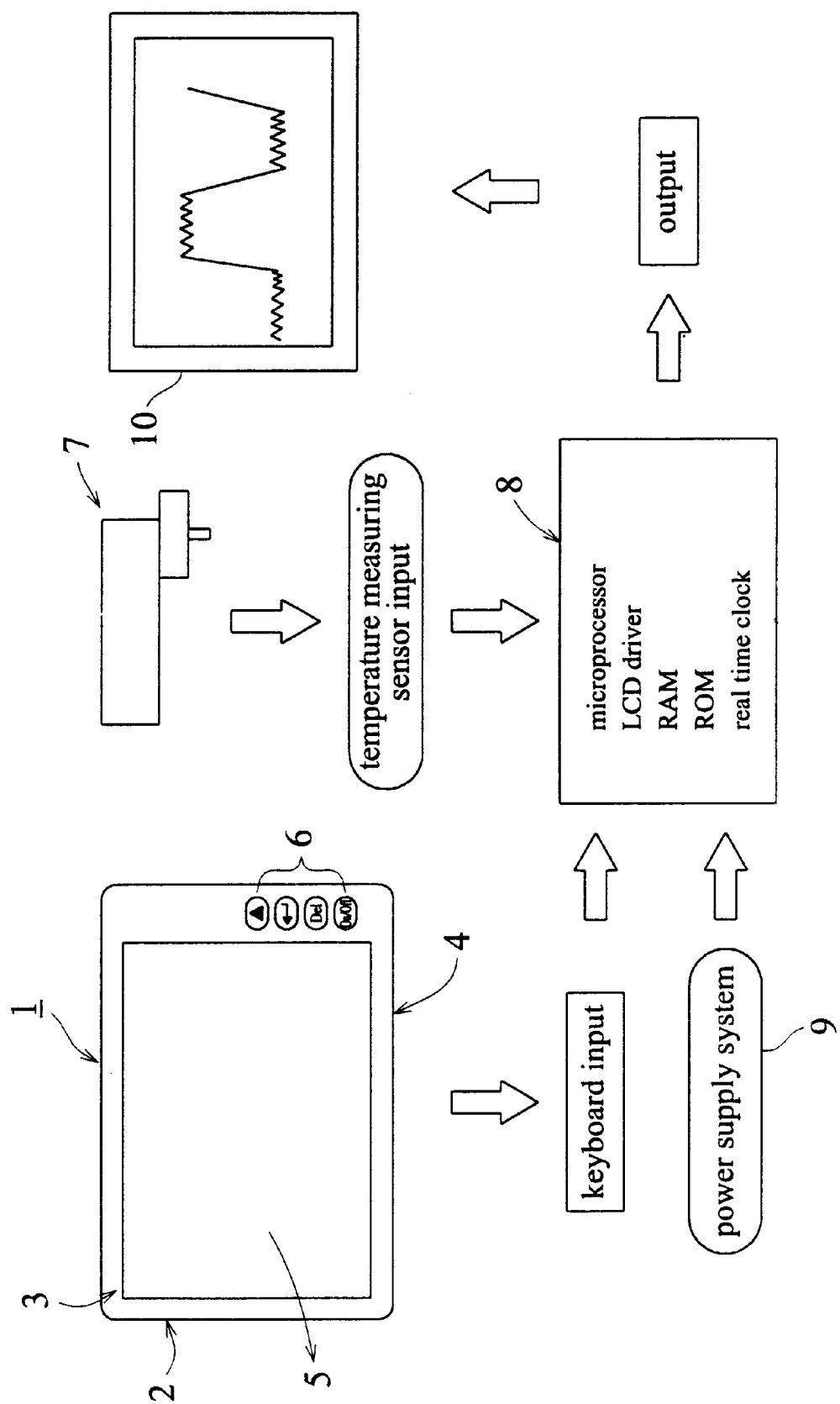
FIG. 2 is a schematic diagram showing general features of the indicating device for menstruation of the present invention.

FIG. 2 generally illustrates the indicating device for menstruation 1 of the present invention and electronic features thereof. The indicating device for menstruation 1 includes a housing 2 having a front panel 3 and a back panel 4. The front panel 3 presents an LCD (liquid crystal diode) display window 5 and a keyboard 6 of the indicating device for menstruation 1. The keyboard 6 bears an on/off key (On/Off), an up key (▲), a delete key (Del), and an enter key (↵).

As shown in FIG. 2, the indicating device for menstruation 1 comprises a temperature measuring sensor 7. In one embodiment of the present invention, the temperature measuring sensor 7 is a tympanic thermometer. Basal body temperatures measured by a tympanic thermometer are more representative of the real body temperatures than conventional axillary temperatures or oral temperatures. It is easier to measure tympanic temperatures than conventional vaginal temperatures or rectal temperatures, and they are more hygienic and more acceptable to women. Besides, measuring basal body temperatures by a tympanic thermometer is also faster than other methods.

As represented generally at 8 in FIG. 2, the microcomputer 8 of the indicating device for menstruation 1 includes a microprocessor, an LCD display driver, an RAM (random access memory), an ROM (read only memory) and a real time clock. The power of the indicating device for menstruation 1 is supplied by the power supply system 9.

FIG. 2 also generally illustrates the LCD display 10, which is responsive to the variable function selections and displays it. For example, the LCD display 10 of FIG. 2 may display the graph of daily changes in body temperatures shown in FIG. 1.

The microcomputer 8 of the indicating device for menstruation 1 of the present invention uses a mathematical method to estimate the user's monthly gynecophysiological factors. The mathematical method includes weighting coefficients, in which the weighting coefficients are determined according to the following three principles: (1) The weighting coefficient of the newest record is the largest, and the older the historical parameters are, the lesser will be their weighting coefficients; (2) Those which deviate more from the normal range have lesser weighting coefficients whereas those within the normal range have the same weighting coefficients; (3) When specific events are confirmed by the user, the weighting coefficients obtained by the system will be 0.

In one embodiment of the present invention, the following equations are used to calculate weighting coefficients (Wi), in which MCD implies menstrual period, and subscripts (i−1) and i respectively implies monthly data sets (i−1) and i which are counted ahead of this month:

If $ABS(MCD_{i-1} - MCD_i) < 4$, $$W_i = \{1 - ABS(MCD_{i-1} - MCD_i)/MCD_{i-1}\} \times (0.8)^i;$$

If $4 < ABS(MCD_{i-1} - MCD_i) \leq 10$, $$W_i = 0.6\{1 - ABS(MCD_{i-1} - MCD_i)/MCD_{i-1}\} \times (0.8)^i; \text{ and}$$

If $10 < ABS(MCD_{i-1} - MCD_i)$, or certain events have been confirmed by the user, $$W_i = 0.$$

According to these equations, the microcomputer 8 of the indicating device for menstruation 1 of the present invention is capable of estimating the user's monthly gynecophysiological factors, which include the menstrual period ($MCD_{0e}$), the menstrual commence day ($MD_{0e}$), the day that the basal body temperature changes ($BB_{0e}$), the starting day and ending day of basal body temperature measurements ($BTB_{0e}$ & $BTE_{0e}$), the ovulation day ($OD_{0e}$), the starting day and ending day of possible ovulation ($OB_{0e}$ & $OE_{0e}$), and the starting day and ending day of the fertility period ($PB_{0e}$ & $PE_{0e}$). The calculation is done according to the following equations, in which i=1~3. $MD_1$ implies the last menstrual commence day, the subscript 0 implies the newest data input in this month, the subscript 0e is the estimated value of this month, and CB and CE respectively implies the starting day and ending day of vaginal mucus:

$$MCD_{0e} = \Sigma W_i \times MCD_i \Sigma EW_i, \text{ or}$$

$$MCD_{0e} = (-0.08) \times (\text{the age of a woman}) + (29.66)$$

when without historical $MCD_i$;

$$MD_{0e} = (MD_1 + MCD_{0e}) \text{ or } \{(MD_1 + MCD_{0e}) - (\text{the days of the month})\};$$

$$BB_{0e} = \Sigma W_i \times BB_i / \Sigma W_i;$$

$$BTB_{0e} = BB_{0e} - 8;$$

$$BTE_{0e} = BB_{0e} + 4;$$

$$OD_{0e} = MCD_{0e} - \{\Sigma W_i \times (MCD_i - BB_i) / \Sigma W_i\};$$

$$OB_{0e} = CB_{0e} = \Sigma W_i \times CB_i / W_i \text{ or } CB_0, \text{ or}$$

$$OB_{0e} = (0.68) \times MCD_{0e} - 8.64$$

when without historical $CB_i$;

$$OE_{0e} = CE_{0e} = \Sigma W_i \times CE_i / \Sigma W_i \text{ or } CE_0;$$

$$PB_{0e} = \{\min(MCD_i) - 18\} \times \{MCD_{0e} / \min(MCD_i)\}; \text{ and}$$

$$PE_{0e} = \{\max(MCD_i) - 11\} \times \{MCD_{0e} / \max(MCD_i)\}, \text{ or}$$

$$PE_{0e} = BB_0 + 3\{(BB_{0e} + 3) \text{ before } BB_0 \text{ is input}\}, \text{ or}$$

$$PE_{0e} = CE_0 + 4\{(CE_{0e} + 4) \text{ when without CE0 input}\};$$

Figure 3:
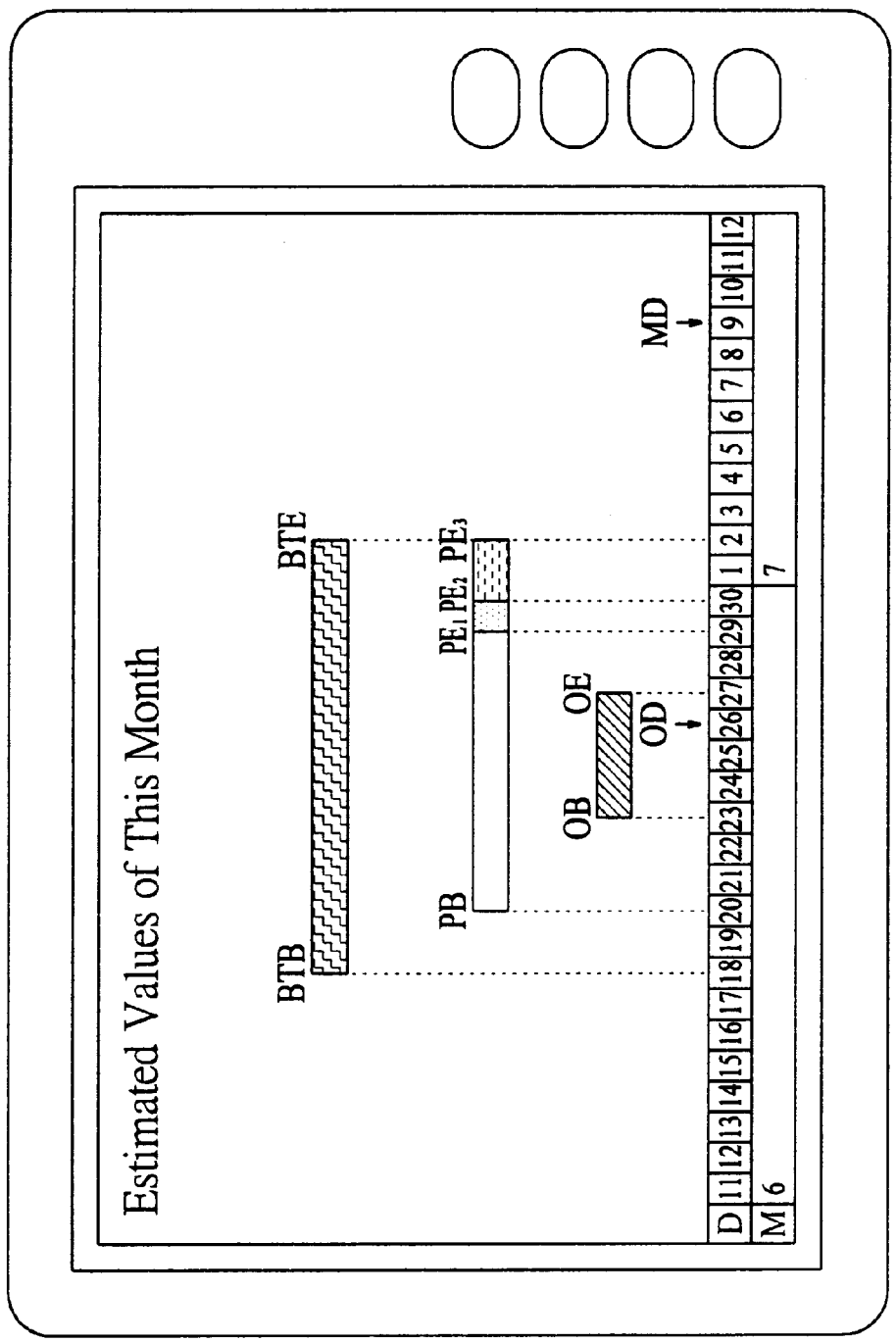
FIG. 3 is a graph showing one displayed function of the indicating device for menstruation of the present invention.

FIG. 3 is showing one displayed function of the indicating device for menstruation 1 of the present invention. The microcomputer 8 of the indicating device for menstruation 1 of the present invention uses the above equations to calculate gynecophysiological factors of a woman from June to July. As shown in FIG. 3, the woman's estimated starting day and ending day of basal body temperature measurements ($BTB_{0e}$ & $BTE_{0e}$) are respectively June 18 and July 2; the estimated starting day of the fertility period ($PB_{0e}$) is June 20; the estimated ending day of the fertility period ($PE_{0e}$) is June 29, June 30 or July 2 depending on the extent of safety; the estimated starting day and ending day of possible ovulation ($OB_{0e}$ & $OE_{0e}$) are respectively June 23 and June 27; the estimated ovulation day ($OD_{0e}$) is June 26; and the estimated next menstrual commence day ($MD_{0e}$) is July 9.

Figure 4:
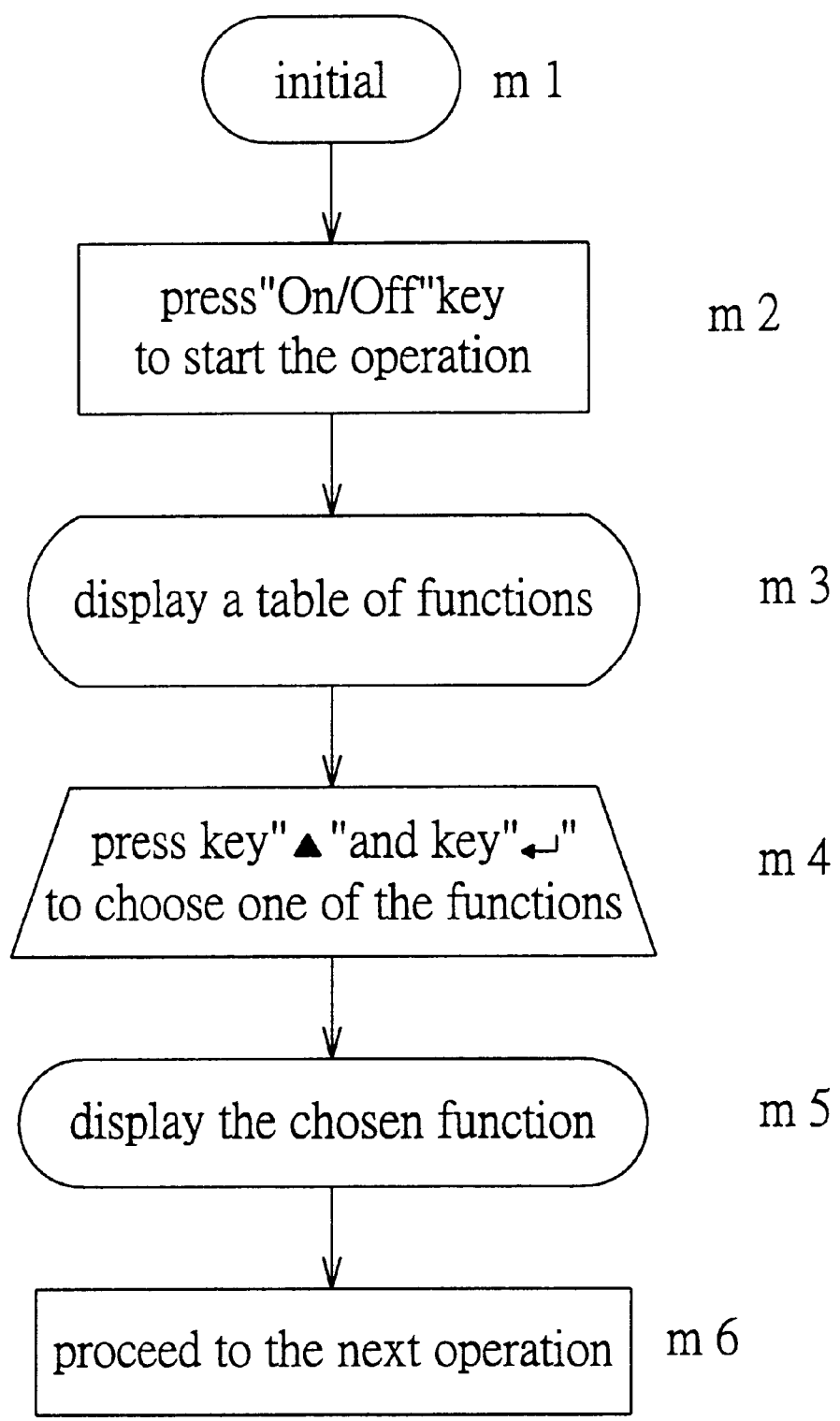
FIG. 4 is a flowchart showing an example of operating the indicating device for menstruation of the present invention.

FIG. 4 is a flowchart showing an example of operating the indicating device for menstruation of the present invention. In FIG. 4, the indicator is initialed in Step m1, and the process proceeds to Step m2. In Step m2, the user starts the operation by pressing the key "On/Off" shown in FIG. 2. Thereafter, in Step m3, a table of functions is displayed on the LCD display 10 shown in FIG. 2. In Step m4, the user chooses one of the functions by pressing key "▲" and then key "↵". In Step m5, the LCD display 10 displays the function chosen. For example, if the function of "Display the Graph of Body Temperature" is chosen in Step m4, then the graph of daily changes in body temperatures shown in FIG. 1 is displayed on LCD display 10 in Step m5; if the function of "Display the Estimated Values of This Month" is chosen in Step m4, then the graph of estimated values of this month shown in FIG. 3 is displayed on LCD display 10 in Step m5. In Step m6, the user may proceed to the next operation.

While the present invention has been described with reference to the specific embodiments, the description is only illustrative and is not to be construed as limiting the invention. Various modifications and applications can be made without departing from the spirit and scope of the following claims.

What is claimed is:

1. A method for determining menstrual factors using a microprocessor, the method comprising the steps of:

inputting a plurality of menstrual data into said microprocessor;

determining a plurality of weighting factors ($W_i$) that respectively correspond to said plurality of menstrual data; and using said plurality of weighting factors to calculate at least one estimated menstrual factor.

2. A method for determining menstrual factors as claimed in claim 1, wherein said plurality of menstrual data comprises a plurality of menstrual commencement days, and further comprising the step of thereby determining at least one menstrual period.

3. A method for determining menstrual factors as claimed in claim 2, wherein said plurality of weighting factors ($W_i$) are determined according to the following equations, in which the abbreviation ABS stands for absolute value, $MCD_i$ and $MCD_{i-1}$ are menstrual periods, subscripts i and i−1 represent monthly data sets containing previous months' data, n and m are predetermined coefficients, $n \leq 1$, and $m < 1$:

if $ABS(MCD_{i-1} - MCD_i) \leq 4$, then $W_i = \{1 - ABS(MCD_{i-1} - MCD_i)/MCD_{i-1}\} \times n^i$;

if $4 < ABS(MCD_{i-1} - MCD_i) < 10$, then $W_i = m\{1 - ABS(MCD_{i-1} - MCD_i)/MCD_{i-1}\} \times n^i$; and if $10 < ABS(MCD_{i-1} - MCD_i)$, or certain events have been confirmed by a user, then $W_i = 0$.

4. A method for determining menstrual factors according to claim 2, wherein said menstrual factors comprise at least some of the following factors: a menstrual period ($MCD_{0e}$), a menstrual commencement day ($MD_{0e}$), a day that a basal body temperature changes ($BB_{0e}$), a starting day ($BTB_{0e}$) and an ending day ($BTE_{0e}$) of basal body temperature measurements, an ovulation day ($OD_{0e}$), a starting day ($OB_{0e}$) and an ending day ($OE_{0e}$) of possible ovulation, a starting day ($PB_{0e}$) and ending day ($PE_{0e}$) of a fertility period, a starting day (CB) and an ending day (CE) of vaginal mucus, said menstrual factors being determined in accordance with the following equations:

$$MCD_{0e} = \Sigma W_i \times MCD_i / \Sigma W_i, \text{ or,}$$

when without historical menstrual period data $MCD_i$, $$MCD_{0e} = a \times (\text{the age of a woman}) + b;$$

$$MD_{0e} = (MD_1 + MCD_{0e}) \text{ or } \{(MD_1 + MCD_{0e}) - (\text{the days of the month})\};$$

$$BB_{0e} = \Sigma W_i \times BB_i / \Sigma W_i;$$

$$BTB_{0e} = BB_{0e} - 8;$$

$BTE_{0e} = BB_{0e} + 4;$ $OD_{0e} = MCD_{0e} - \{\Sigma W_i \times (MCD_i - BB_i)/\Sigma W_i\};$ $OB_{0e} = CB_{0e} = \Sigma W_i \times CB_i/\Sigma W_i$ or $CB_0$, or, when without historical mucus starting day data, $OB_{0e} = c \times MCD_{0e} + d;$ $OE_{0e} = CE_{0e} = \Sigma W_i \times CE_i/\Sigma W_i$ or $CE_0;$ $PB_{0e} = \{min(MCD_i) - 18\} \times \{MCD_{0e}/min(MCD_i)\};$ and $PE_{0e} = CE_0 + 4$, or $PE_{0e} = CE_{0e} + 4$ when without $CE_0$ input, where $i = 1 \sim p$, $1 < p \leq 12$; $a < 0$; $b > 24$; $c < 1$; $d < 0$; $MD_1$ represents a last menstrual commencement day, subscript 0 represents a newest input data for a current month, and subscript 0e represents an estimated value for the current month.

5. A method for determining menstrual factors according to claim 2, wherein said certain events are selected from the group consisting of taking hormone medicines, serious illnesses, or emotional fluctuations.

* * * * *